US012150933B2

(12) United States Patent
Allegretti et al.

(10) Patent No.: US 12,150,933 B2
(45) Date of Patent: Nov. 26, 2024

(54) IL-8 INHIBITORS FOR USE IN THE TREATMENT OF SOME UROLOGICAL DISORDERS

(71) Applicant: DOMPÉ FARMACEUTICI S.P.A., Milan (IT)

(72) Inventors: Marcello Allegretti, Rome (IT); Andrea Aramini, L'Aquila (IT); Maria Candida Cesta, L'Aquila (IT); Gianluca Bianchini, L'Aquila (IT); Laura Brandolini, L'Aquila (IT); Patrizia Angelico, Sesto San Giovanni (IT)

(73) Assignee: DOMPÈ FARMACEUTICI S.P.A., Milan (IT)

( * ) Notice: Subject to any disclaimer, the term of this patent is extended or adjusted under 35 U.S.C. 154(b) by 401 days.

(21) Appl. No.: 15/743,721

(22) PCT Filed: Jul. 12, 2016

(86) PCT No.: PCT/EP2016/066511
§ 371 (c)(1),
(2) Date: Jan. 11, 2018

(87) PCT Pub. No.: WO2017/009323
PCT Pub. Date: Jan. 19, 2017

(65) Prior Publication Data
US 2018/0200231 A1 Jul. 19, 2018

(30) Foreign Application Priority Data
Jul. 14, 2015 (EP) .................................... 15176726

(51) Int. Cl.
| | | |
|---|---|---|
| *A61K 31/426* | (2006.01) | |
| *A61K 31/165* | (2006.01) | |
| *A61K 31/381* | (2006.01) | |
| *A61K 31/407* | (2006.01) | |
| *A61K 31/664* | (2006.01) | |
| *A61K 31/675* | (2006.01) | |
| *A61K 31/704* | (2006.01) | |
| *A61K 45/06* | (2006.01) | |
| *A61P 13/10* | (2006.01) | |

(52) U.S. Cl.
CPC .......... *A61K 31/426* (2013.01); *A61K 31/165* (2013.01); *A61K 31/381* (2013.01); *A61K 31/407* (2013.01); *A61K 31/664* (2013.01); *A61K 31/675* (2013.01); *A61K 31/704* (2013.01); *A61K 45/06* (2013.01); *A61P 13/10* (2018.01); *A61K 2300/00* (2013.01)

(58) Field of Classification Search
CPC .. A61K 31/426; A61K 31/165; A61K 31/381; A61K 31/407; A61K 31/664; A61K 31/675; A61K 31/704; A61K 45/06; A61K 2300/00; A61P 13/10
See application file for complete search history.

(56) References Cited

U.S. PATENT DOCUMENTS 5,886,044 A * 3/1999 Widdowson ........... A61K 31/17
514/596
2010/0166739 A1* 7/2010 Chancellor ........ G01N 33/6869
424/130.1

FOREIGN PATENT DOCUMENTS

| WO | WO 2005/068460 | | 7/2005 | | |
|---|---|---|---|---|---|
| WO | WO-2005068460 A1 | * | 7/2005 | .......... | C07D 275/03 |
| WO | WO 2005/090295 A2 | | 9/2005 | | |
| WO | WO-2010031835 A2 | * | 3/2010 | .............. | A61P 13/12 |
| WO | WO 2010/078403 A2 | | 7/2010 | | |

OTHER PUBLICATIONS

Hopkin (Year: 2004).*
Chao (Year: 2007).*
PubChem CID 3854666 (Year: 2005).*
Zhaofei, Scifinder Scholar Abstract Translation (Year: 2013).*
Zhaofei, SciFinder Abstract Translation (Year: 2013).*
Clemons (Year: 2011).*
Urbahns (Year: 2011).*
Dechecchi et al (Year: 2012).*
Nordling et al (Year: 2008).*
Kuschert et al (Year: 1999).*
Stilwell et al (Year: 1988).*
Takahashi et al (Year: 2013).*
Sarbjinder et al (Year: 2004).*
Nordling (Year: 2008).*
Kuschert (Year: 1999).*
Stillwell (Year: 1988).*
Takahashi (Year: 2013).*
Dornelles (Year: 2014).*
Hipkin (Year: 2004).*
Sarbjinder (Year: 2004).*
Allegretti, et al, Immunology Letters, vol. 145, p. 68-78, 2012.
Bertini, et al., British Journal of Pharmacology, vol. 165, p. 436-454, 2012.
Buchbinder, et al, Journal of Clinical Epidemiology, vol. 53, p. 1013-1019, 2000.
Busch-Petersen, Current Topics in Medicinal Chemistry, vol. 6, p. 1345-1352, 2006.
Chao, et al., Bioorganic and Medicinal Chemistry Letters, vol. 17, p. 3778-3783, 2007.
Chapman, et al., Pharmacology and Therapeutics, vol. 121, p. 55-68, 2009.

(Continued)

*Primary Examiner* — Jeffrey S Lundgren
*Assistant Examiner* — Ibrahim D Bori
(74) *Attorney, Agent, or Firm* — HUESCHEN AND SAGE

(57) ABSTRACT

The present invention relates to IL-8 inhibitor compounds, preferably dual CXCR1/CXCR2 receptor inhibitors, useful in the treatment and/or prevention of interstitial cystitis/painful bladder syndrome (IC/PBS) and/or over active bladder (OAB), also including IC/PBS and/or OAB induced by anticancer therapy. Methods of treatment and/or prevention, combinations and kits comprising said IL-8 inhibitors are also covered therein.

17 Claims, 6 Drawing Sheets

(56) References Cited

OTHER PUBLICATIONS

Chuntharapai, et al., The Journal of Immunology, vol. 155, p. 2587-2594, 1995.
Denton, AS, et al., Cochrane Database of Systematic Reviews, Issue 3, Art. No. CD001773, 2002.
Dornells, et al., British Journal of Pharmacology, vol. 171, p. 452-467, 2014.
Fincham, et al., The Journal of Immunology, vol. 140, No. 12, p. 4294-4299, Jun. 15, 1988.
Godaly, et al., Journal of Leukocyte Biology, vol. 69, p. 899-906, Jun. 2001.
Gormley, et al., AUA/SUFU Guideline, "Diagnosis and Treatment of Overactive Bladder (Non-Neurogenic) in Adults", Feb. 2014.
Griffin, et al., Arch Dermatol, vol. 124, p. 216-220, Feb. 1988.
Hall, et al., The Journal of Urology, vol. 178, p. 2314-2330, Dec. 2007.
Hanno, et al., American Urological Association Guideline, Diagnosis and Treatment of Interstitial Cystitis/Bladder Pain Syndrome, Jul. 2013.
International Search Report for PCT/EP2016/066511 on Sep. 7, 2016.
Isaka, et al., Cancer Chemotherapy Pharmacology, vol. 30 (Suppl), p. S 41-S 44, 1992.
Jeffery, Peter K. Thorax, vol. 53, p. 129-136, 1998.
Jie Jack Li, Expert Opinion Ther. Patents, vol. 11, No. 12, p. 1905-1910, 2001.
Jones, et al., Journal of Biological Chemistry, vol. 272, No. 26, p. 16166-16169, Jun. 27, 1997.
Jones, et al., Procedings of National Acadamy of Science, vol. 93. p. 6682-6686, Jun. 1996.
Juszczak, et al., Folia Medica Cracoviensia, vol. XLVIII 1-4, p. 113-123, 2007.
Lamm, et al., European Urology, vol. 57, p. E7-E9, 2010.
Lee, et al., The Journal of Biological Chemistry, vol. 267, No. 23, p. 16283-16287, Aug. 15, 1992.
Lefer, et al., Brittish Journal of Pharmacology, vol. 103, p. 1153-1159, 1991.
Paliez, et al., The Journal of Biological Chemistry, vol. 276, No. 5, p. 3090-3097. Feb. 2, 2001.
Pesci, et al., European Respiratory Journal, vol. 12, p. 380-386, 1998.
Premont, et al., Annual Review of Physiology, vol. 69, p. 511-534, 2007.
Raghuwanshi, et al., Journal of Immunology, vol. 189, No. 6, p. 2824-2832, Sep. 15, 2012.
Richardson, et al. The Journal of Biological Chemistry, vol. 273, No. 37, p. 23830-23836, Sep. 11, 1998.
Richardson, et al., The Journal of Immunology, vol. 170, p. 2904-2911, 2003.
Romson, et al., American Heart Association Circulation, vol. 67, p. 1016-1023, 1983.
Santos, et al., Naunyn-Schmied Arch Pharmacology, vol. 382, p. 399-407, Sep. 1, 2010.
Sekido, et al., Letters To Nature, vol. 365, p. 654-657, Oct. 14, 1993.
Stillwell, et al., Cancer, vol. 61, No. 3, p. 451-457, Feb. 1, 1988.
Takematsu, et al., Arch Dermatol, vol. 129, p. 74-80, Jan. 1993.
Tseng-Rogenski, et al., American Journal Physiol Renal Physiology, vol. 297, p. F816-F821, Jun. 11, 2009.
Welbourn, et al., British Journal of Surgery, vol. 78, No. 6, p. 651-655, Jun. 1991.
Wolf, et al., European Journal of Immunology, vol. 28, p. 164-170, 1998.
Zhi Liu, et al., The Journal of Clinical Investigation, vol. 100, No. 5, p. 1256-1263, Sep. 1997.
Abdel-Mageed, Urol Res (2003) 31: 300-305.
Dí Capua-Sacoto, et al., Actas Urol Esp. (2018) 42: 262-266.
Shie, et al., BJU International (2011) 108: E136-E141.
Shie, et al., Tzu Chi Med J (2009) 21: 103-109.
Foster, Jr., et al., J Urol. May 2010: 183(5): 1853-1858.
Generali, et al., Hosp Pharm 2014;49(9):809-810.
Matsushima, et al., Cytokine, vol. 1, No. 1, Nov. 1989:2-13.
Glynn et al., Eur. Respir. J., 2001, 18, 522-529.
Hammond et al., J. Immunol., 1995, 155, 1428-1433.

* cited by examiner

IL-8 INIHIBITORS FOR USE IN THE TREATMENT OF SOME UROLOGICAL DISORDERS

TECHNICAL FIELD

The present invention relates to IL-8 inhibitor compounds for use in the treatment of interstitial cystitis/painful bladder syndrome (IC/PBS) and/or over active bladder (OAB), also including IC/PBS and/or OAB induced by anticancer therapy.

BACKGROUND ART

IC/PBS and OAB are chronic inflammatory diseases of the urinary tract characterized by persistent inflammatory processes in the tissue. Symptoms of these diseases vary, however the more common symptoms are mild discomfort, pressure, tenderness, or intense pain in the pelvic area. Symptoms may also include an urgent need to urinate, frequent need to urinate, urgency incontinence or a combination of these symptoms; pain may change in intensity as a bladder fills with urine or as it empties.

AUA has released guidelines setting out objective criteria for the diagnosis of IC/PBS (Diagnosis and Treatment of Interstitial Cystitis/Bladder Pain Syndrome AUA Guidelines 2011, amended in 2014) and OAB (Diagnosis and Treatment of Overactive Bladder (Non-Neurogenic) in adults: AUA/SUFU Guideline 2014) Multiple approaches are available to treat these pathologies, often used in combination. Interventions may include: oral pharmacologic agents [e.g., pentosan polysulfate sodium (PPS, Elmiron), anticholinergic drugs (such as amitriptyline), histamine-receptor antagonists (such as hydroxyzine), tricyclic antidepressants, analgesics, anti-inflammatory agents, immunosuppressive agents (such as cyclosporine A]; intravesical therapies via catheter including dimethylsulfoxide (DMSO), PPS, neurotoxins, hyaluronic acid, chondroitin sulphate, electrical stimulation, and complementary therapies (e.g. acupuncture, hypnosis). However, the available treatments are largely insufficient because of their limited efficacy and/or side effects and a need still exists for the identification of more effective and safer medicaments for the treatment of IC/PBS and/or OAB.

Chemokines constitute a large family of chemotactic cytokines that exert their action via an interaction with receptors belonging to the seven Transmembrane G Protein Coupled Receptor (7TM-GPCRs) family. The chemokine system is crucial for the regulation and the control of the basal homeostatic and inflammatory leukocyte movement. Many cell types, besides the hematopoietic cells, express chemokine receptors; they include endothelia, smooth muscle cells, stromal cells, neurons and epithelial cells.

Among chemotactic factors, Interleukin-8 (IL-8; CXCL8) is considered a major mediator of PMN (Polymorphonuclear Neutrophils) recruitment and involved in several pathologies including psoriasis, rheumatoid arthritis, chronic obstructive pulmonary disease and reperfusion injury in transplanted organ (Griffin et al, Arch Dermatol 1988, 124: 216; Fincham et al, J Immunol 1988, 140: 4294; Takematsu et al, Arch Dermatol 1993, 129: 74; Liu et al, 1997, 100:1256; Jeffery, Thorax 1998, 53: 129; Pesci et al, Eur Respir J. 1998, 12: 380; Lafer et al, Br J Pharmacol. 1991, 103: 1153; Romson et al, Circulation 1993, 67: 1016; Welbourn et al, Br J Surg. 1991, 78: 651; Sekido et al, Nature 1993, 365, 654).

The biological activity of Interleukin-8 is mediated by the interaction with the CXCR1 and CXCR2 receptors belonging to the 7TM-GPCR family, that are expressed on the surface of human PMNs. The two human receptors are highly homologous (77% aminoacid identity), and the greatest diversity is focused at three regions: the N terminus (the ligand-binding region), the fourth transmembrane domain and the C terminus [Lee et al, J Biol Chem 1992, 267: 16283].

While human CXCR1 is quite selective, binding with high affinity only two chemokines, IL-6 and IL-8, and showing a much higher affinity for IL-8 [Wolf et al, Eur J Immunol 1998, 28: 164], human CXCR2 a is a more promiscuous receptor, binding a number of different cytokines and chemokines in addition to the two above, such as for example IL-1, IL-2, IL-3, IL-5, and IL-7 (Chapman et al., Pharmacology & Therapeutics 121 (2009) 55). Therefore, CXCR2 mediates the activity of a number of different mediators.

For both receptors, following activation the responses are regulated by phosphorylation at specific residues of the C-terminus that causes the association with an heterotrimeric G-protein complex which dissociates into its subunits to stimulate effector molecules and, thereby, causes activation of phospholipase C, resulting in the generation of the intracellular messenger diacylglycerol and inositol 1,4,5-triphosphate.

Following CXCL8 activation, CXCR1 and CXCR2 become desensitized and downregulated by internalization of the receptor (Richardson et al, J Biol Chem 1998; 273: 23830 Richardson et al, J Immunol. 2003, 170: 2904; Premont et al, Annu Rev Physiol 2007, 69: 511).

CXCR1 and CXCR2 are phosphorylated via two main mechanisms: a protein kinase C-dependent mechanism and a GRK (GPCR kinase)-dependent mechanism. For example, the C-terminal tail phosphorylation of CXCR1 is required for processes such as chemotaxis and receptor internalization. It has been shown that the two receptors, CXCR1 and CXCR2, are coupled to different intracellular pathways through the interaction with distinct GRK isoforms. In particular, CXCR1 predominantly couples to GRK2, whereas CXCR2 interacts with GRK6 to negatively regulate receptor sensitization and trafficking, thus affecting cell signaling and angiogenesis (Raghuwanshi et al, J Immunol 2012, 189: 2824). Upon IL-8 activation, CXCR1 slowly internalizes (45% after 60 min) but recovers rapidly (100% after 90 min), whereas CXCR2 internalizes rapidly (95% after 10 min) but recovers slowly (35% after 90 min) at the cell surface [Richardson et al, J Immunol 2003, 170: 2904; Chuntharapai et al, J Immunol 1995, 1995, 155: 2587]. This distinction appears critical in the ability of the two receptors to activate specific leukocyte responses, including respiratory burst and postendocytic signals. Despite evidence that the two receptors signal through similar G proteins, there are marked differences in the activation of signaling cascade between CXCR1 and CXCR2, which identifies diverse functions. For example, inhibition of CXCR1 but non CXCR2 causes a decrease in superoxide anion production by PMNs, indicating a pivotal role of CXCR1 in oxidative burst [Jones et al, J Biol Chem 1997, 272: 16166; Jones et al, PNAS USA 1996, 93: 6682]. In addition, CXCR1 activates PLD1 (phospholipase D1), whereas CXCR2 mediates PLD2 (phospholipase D2) activation that catalyzes the hydrolysis of phosphatidylcholine to phosphatidic acid and choline [Palicz et al, J Biol Chem 2001, 276: 3090].

A number of studies have investigated the role of IL-8 in urological disorders. WO2010/078403 discloses that a number of cytokines, chemokines and growth factors, including IL-8, are increased in the urine of patients affected by urological disorders and hypothesizes that the identification of elevated concentrations of these proteins in the urine can be used as a diagnostic tool. Multiple proteins are identified in the document as potential biomarkers of urological pathologies, all of these being well known inflammation mediators.

Jiang et al disclose increased levels of pro-inflammatory cytokines and chemokine including IL-1β, IL-6, TNF-α, and IL-8, as well as serum C-reactive protein (CRP), nerve growth factor (NGF) in patients with IC/PBS compared to controls (PlosOne 2013, 10: e76779). The above documents teach that IC/PBS is associated with the presence in the urine or serum of the patients of a number of mediators of inflammation, including IL-8, but do not provide any teaching as regards the specific role of each of these mediators in the onset and progression of the disease. Furthermore, the documents lack any information on the effect of inhibition of the identified potential markers on the onset and/or progression of urological disorder.

Some publications disclose data that suggests that IL-8 and CXCR1 have an important role in the maintenance of the health of the urinary tract.

In fact, it has been demonstrated that IL-8 exerts a protective effect of on the urothelium and that lower IL-8 expression levels in the urinary bladder may contribute to pathophysiology of interstitial cystitis and other urological disorders [Tseng-Rogenski et al, Am J Physiol Renal Physiol 2009, 297: F816-F821]. In this publication, IL-8 is described as a growth factor essential for normal urothelial tissue survival. In particular, it has is shown that the inhibition of IL-8 expression by small inhibitory RNA (siRNA) causes normal urothelial cells to die and that the addition of recombinant human IL-8 rescues the treated cells. Furthermore, in this study the levels of IL-8 mRNA are measured in biopsy samples from bladder and lower IL-8 levels are observed in biopsies from patients with interstitial cystitis. On the basis of the data obtained, it is suggested that IL-8 and/or agents that stimulate IL-8 production may be potential therapeutic agents for the treatment of interstitial cystitis.

A further study has shown a lower expression of CXCR1, but not of CXCR2, in children with recurrent history of Urinary Tract Infections (UTI) compared to healthy children (Godaly, Journal of Leukocytes Biology 2001, 69, pages 899-906).

Recently, the selective blockade of CXCR2 receptor has been shown to exert a beneficial effect in a model of interstitial cystitis, with an increase in bladder capacity voiding volume and efficiency and a decrease in bladder pressure and mechanical hypersensitivity. However, the different molecular ligands acting on the receptor and, by consequence, the intracellular pathways whose inhibition is at the basis of this effect have not yet been fully elucidated [Dornelles et al, Br J Pharmacol. 2014, 171:452].

As regards IL-8, the above described documents suggest that this chemokine and, in particular, its activity through CXCR1 receptor, plays a pivotal role in normal urothelial cell survival and that a decreased level of expression of IL-8 or CXCR1 in the urinary bladder contributes to the pathophysiology of urinary disorders. Furthermore, they suggest different and opposite roles of CXCR1 and CXCR2 in IC/PBS and OAB.

SUMMARY OF INVENTION

Surprisingly, the Applicant has now found that, in contrast with the teaching of the prior art, inhibitors of IL-8, are useful in the treatment and/or prevention of IC/PBS and/or OAB, also including IC/PBS and/or OAB induced by anticancer therapy. Accordingly, the first object of the present invention is an IL-8 inhibitor, preferably an antibody or small molecule, for use in the treatment and/or prevention of IC/PBS and/or OAB.

The second object of the present invention is the use of said IL-8 inhibitor as defined above, for the preparation of a medicament for the treatment and/or prevention of IC/PBS and/or OAB.

The third object of the present invention is a method for the treatment and/or prevention of IC/PBS and/or OAB, also including IC/PBS and/or OAB induced by anticancer therapy, in a subject comprising the step of administering to the subject in need thereof a therapeutically effective amount of said IL-8 inhibitor.

The fourth object of the present invention is a pharmaceutical formulation for use in the treatment and/or prevention of IC/PBS and/or OAB comprising (a) an IL-8 inhibitor as defined above and (b) one or more further pharmaceutically active compounds.

The fifth object of the present invention is a kit for use in the treatment and/or prevention of IC/PBS and/or OAB, comprising an IL-8 inhibitor as defined above and one or more pharmaceutically active compounds for simultaneous, separate or sequential use.

FIGURE DESCRIPTION

FIG. 1 shows the effect of oral administration of vehicle, Compound 1 (Compd. 1) and Compound 2 (Compd. 2), administered at a dosage of 10 and 30 mg/kg, on the abdomen mechanical threshold, expressed in grams, tested as described in Example 1. Data represent the withdrawal threshold value before (basal) and after CYP administration, before treatment (pre) and after treatment (post) with Compounds 1 and 2.

Data are expressed as Mean values±S.E. and are reported in logarithmic scale. ***$p<0.001$ versus basal values; °$p<0.05$, °°°$p<0.001$, versus pre-treatment values (one way ANOVA with Tukey's test).

FIG. 2 shows the effect of oral administration of vehicle, Compound 1 (Compd. 1) and Compound 2 (Compd. 2), administered at a dosage of 10 and 30 mg/kg, on the posterior hind paws mechanical threshold, expressed in grams. Data represent the withdrawal threshold value before CYP administration (basal), and after CYP administration, before treatment (pre) and after treatment (post) with vehicle, Compounds 1 or 2, tested as described in Example 1. Data are expressed as Mean values±S.E. and are reported in logarithmic scale.

***$p<0.001$ versus basal values; °°°$p<0.001$ versus pre-treatment values (one way ANOVA with Tukey's test).

FIG. 3 shows the effect of oral administration of vehicle and Comp. 1, administered at a dosage of 1, 3 and 10 mg/kg, on the abdomen mechanical threshold, expressed in grams, tested as described in Example 1. Data represent the withdrawal threshold value before CYP administration (basal); and after CYP administration, before treatment (pre) and after treatment (post) with vehicle or Compound 1. Data are expressed as Mean values±S.E. ***$p<0.001$ versus basal values; °°$p<0.01$, °°°$p<0.001$, versus pre-treatment values (one way ANOVA with Tukey's test).

FIG. 4 shows the effect of oral administration of vehicle and Comp. 1), administered at a dosage of 1, 3 and 10 mg/kg on the hind-paws mechanical threshold, expressed in grams, tested as described in Example 1. Data represent the withdrawal threshold value before CYP administration (basal);

after CYP and before treatment (pre); and after CYP administration, before treatment (pre) and after treatment (post) with vehicle or Compound 1. Data are expressed as Mean values±S.E. ***p<0.001 versus basal values; °°°p<0.001, versus pre-treatment values (one way ANOVA with Tukey's test).

FIG. 5 shows the effect of oral administration of vehicle and Compound 1 (Compd. 1), administered at a dosage of 7 mg/kg on abdomen and the hind-paws mechanical threshold, expressed in grams, tested as described in Example 1. Data represent the withdrawal threshold value before CYP administration (basal); and after CYP administration, before treatment (pre) and after treatment (post) with vehicle or Compound 1 (Compd. 1), as described in Example 1. Data are expressed as Mean values±S.E. ***p<0.001 versus basal values; °°°p<0.001, versus pre-treatment values (one way ANOVA with Tukey's test).

FIG. 6 shows the effect of chronic oral administration of vehicle and Compound 1 (Compd. 1), administered at as dosage of 7 mg/kg, on the abdomen and hind-paws mechanical threshold, expressed in grams, tested as described in Example 2. Data represent the withdrawal threshold value before CYP administration (basal); and after CYP administration, before treatment (pre) and after chronic treatment (p 12) with vehicle or Compound 1, or after chronic treatment+1 acute administration (p13) with Compound 1, as described in Example 2. Data are expressed as Mean values±S.E. p<0.01, *p<0.001 versus basal values; °°°p<0.001, versus pre-treatment values (one way ANOVA with Tukey's test).

Figure 9:
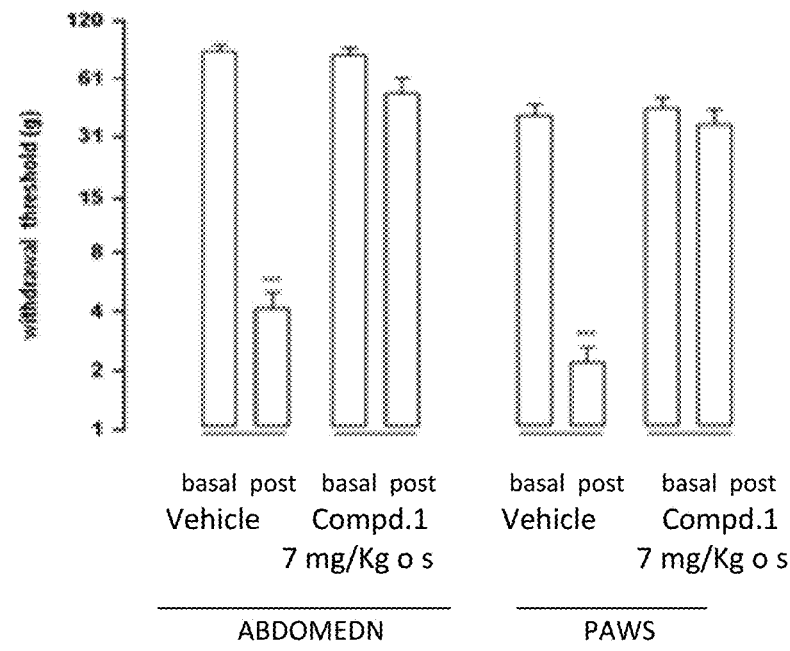
Figure 10:
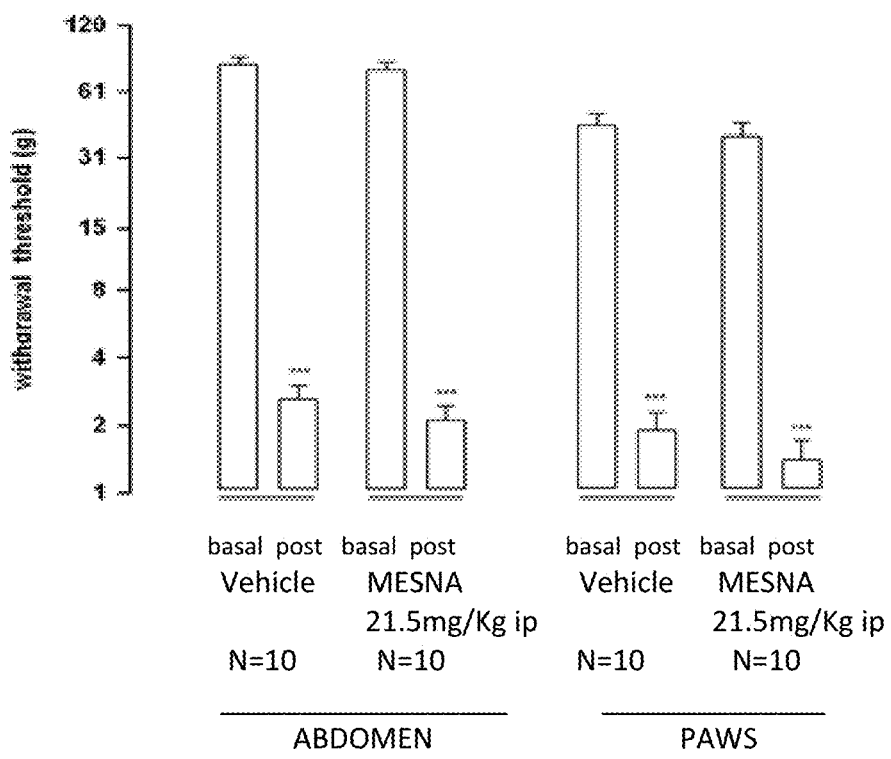

FIG. 9 shows the effect of chronic oral administration of vehicle and Compound 1 (Compd. 1), administered at a dosage of 7 mg/kg, on the abdomen and hind-paws mechanical threshold, expressed in grams. Data represent the withdrawal threshold value before CYP administration (basal) and after CYP administration and after chronic treatment (post) with vehicle or Compound 1, as described in Example 5. Data are expressed as Mean values±S.E FIG. 10 shows the effect of chronic oral administration of vehicle and Mesna, administered at a dosage of 21.5 mg/kg, on the abdomen and hind-paws mechanical threshold, expressed in grams. Data represent the withdrawal threshold value before CYP administration (basal) and after CYP and after chronic treatment (post) with vehicle or Compound 1, as described in Example 5. Data are expressed as Mean values±S.E.

Figure 11:
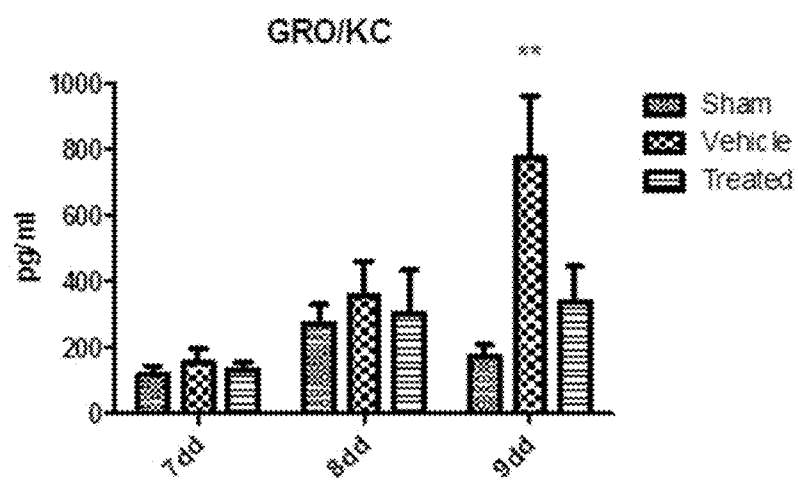

FIG. 11 shows time dependent changes in blood GROa/KC content following CYP administration and effect of the pre-treatment with Compound 2 (Compd 2), administered ad a dosage of 7 mg/kg p.o., as described in Example 7. Each column represents the mean±SEM of 10 animals. * p<0.05;  p<0.01; * p<0.001 versus Sham group, two-way ANOVA with Kruskal-Wallis as post-hoc test.

DETAILED DESCRIPTION OF THE INVENTION

As will be disclosed in details in the Experimental section, small molecules that inhibit the activity of IL-8 have shown therapeutic efficacy in animal models of Interstitial Cystitis, Painful Bladder Syndrome and OAB (Juszczak et al, Folia Med. Cracov 2007, 48 (1-4), p. 113-123).

Accordingly, a first object of the present invention is an IL-8 inhibitor for use in the treatment and/or prevention of IC/PBS and/or OAB.

IC/PBS and OAB can be induced as a collateral effect by anticancer therapy, in particular chemotherapy (Santos et al Naunyn Schmiedebergs Arch Pharmacol. 2010: 382, 399) and radiotherapy to the pelvis (Denton et al Cochrane database Syst Rev, 2002: CD001773).

According to a preferred embodiment of the present invention, also in combination with other embodiments, said IC/PBS and/or OAB are induced by anticancer therapy, such as chemotherapy or radiotherapy to the pelvis.

The term "IL-8-inhibitor" according to the present application refers to any compound able to inhibit, partially or totally, the biological activity of IL-8. Such a compound can act by decreasing the expression or activity of IL-8 or by inhibiting the triggering of the intracellular signaling by activation of the IL-8 receptors. In the latter case, such compound is preferably either an allosteric inhibitor or an antagonist of CXCR1 or of both CXCR1 and CXCR2 receptors. Preferably, said IL-8 inhibitor is able to inhibit chemotaxis induced by IL-8 in PMNs with a concentration in the low microMolar or nanoMolar range.

According to preferred embodiments of the invention, said IL-8 inhibitor is a CXCR1 inhibitor, more preferably it is a dual CXCR1/CXCR2 inhibitor.

According to further preferred embodiments of the invention, also in combination with the preceding embodiments, said IL-8 inhibitor is an antibody, a peptide or small molecule inhibitor.

To date, several IL-8 inhibitors, such as small molecules, peptides and antibodies, have been disclosed, many of which are currently under undergoing clinical trials or are used in therapy. i.e. SK&F 83589, SB225002 (Jie Jack, Expert Opinion Ther. Patents, 2001, 11(12), p. 1905-1910), C(4)-alkyl substituited furanyl cyclobutenediones (Chao J. et al., Bioorganic & Medicinal Chemistry Letters 17, 2007, p. 3778-3783) and different small molecules from GlaxoSmithKline, Astra Zeneca, Pfizer and Schering-Plough (Busch-Petersen J. Current Topics in Medicinal Chemistry, 2006, 6, p. 1345-135 and Allegretti et al, Immunology Letters 2012, Vol. 145, p. 68-78).

Among small molecules inhibitors of IL-8, preferred compounds according to the invention are 1,3-thiazol-2-ylaminophenylpropionic acid derivatives, 2-phenyl-propionic acid derivatives and their pharmaceutically acceptable salts. According to one preferred embodiment, said 2-phenypropionic acid derivatives are compounds of formula (I)

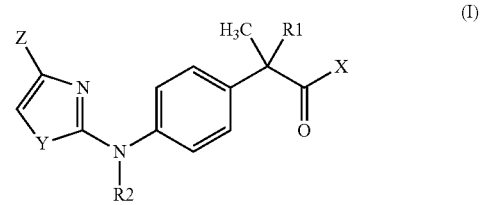

wherein
R1 is hydrogen;
X is OH;
R2 is hydrogen or linear $C_1$-$C_4$ alkyl;
Y is a heteroatom selected from S, O and N;
Z is selected from linear or branched $C_1$-$C_4$ alkyl, linear or branched $C_1$-$C_4$ alkoxy, halo $C_1$-$C_3$ alkyl and halo $C_1$-$C_3$ alkoxy.

More preferably, said compounds of formula (I) have the chiral carbon atom of the phenylproprionic group in the S configuration.

Particularly preferred compounds of formula (I) according to the inventions are selected from (R,S)-2-(4-{[4-(trifluoromethyl)-1,3-thiazol-2-yl]amino}phenyl)propanoic acid or (2S)-2-(4-{[4-(trifluoromethyl)-1,3-thiazol-2-yl]amino} phenyl) propanoic acid and pharmaceutically acceptable salts thereof, preferably a sodium salt. The most preferred 2-aryl-propionic acid derivative according to the invention is the sodium salt of (2S)-2-(4-{[4-(trifluoromethyl)-1,3-thiazol-2-yl] amino} phenyl) propanoic acid (hereinbelow indicated as Compd. 1) Compounds of formula (I) are disclosed in WO2010/031835 which also discloses their method of synthesis, their activity as IL-8 inhibitors as well as their use in the treatment of IL-8 dependent pathologies such as transient cerebral ischemia, bullous pemphigoid, rheumatoid arthritis, idiopathic fibrosis, glomerulonephritis and damages caused by ischemia and reperfusion. Compd. 1 is also specifically disclosed therein and corresponds to compound (3a) of the document.

The present inventors have investigated the pharmacokinetic profile of Compd. 1 and have found that this is particularly advantageous for a use in urinary disorders such as IC/PBS and OAB. In fact, as will be illustrated in the Experimental section, Compd. 1 shows a rapid absorption, reaches a maximum concentration (Cmax) in plasma (47.44±25.43 µg/mL) 2 hr after administration and shows an excellent oral bioavailability. In conclusion, Compd. 1 is well absorbed by the oral route, poorly distributed in the tissues and gradually eliminated from plasma.

According to another preferred embodiment, said 2-phenyl-propionic acid derivative is a compound of formula (II)

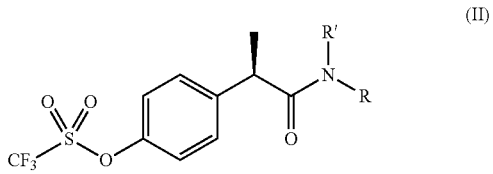

(II)

or a pharmaceutically acceptable salts thereof,
wherein
R' is hydrogen;
R is a residue of formula $SO_2Ra$ wherein Ra is linear or branched $C_1$-$C_4$ alkyl or halo $C_1$-$C_3$ alkyl.

More preferably, said compounds of formula (II) have the chiral carbon atom of the phenylpropionic group in the R configuration.

Even more preferably, the said compound of formula (II) is R(−)-2-[(4'-trifluoromethanesulfonyloxy)phenyl]-N-methanesulfonyl propionamide or a pharmaceutically acceptable salt thereof, preferably a sodium salt. Most preferably said compound of formula (II) is the sodium salt of R(−)-2-[(4'-trifluoromethane sulfonyloxy)phenyl]-N-methanesulfonyl propionamide (hereinbelow indicated as Compd. 2).

2-(R)-Phenyl-propionic acid derivative of formula (II) are disclosed in WO2005/090295; also their method of synthesis, their activity as IL-8 inhibitors as well as their use in the treatment of pathologies like psioriasis, ulcerative colitis, melanoma, chronic obstructive pulmonary diseases (COPD), bullous pemphigo, rheumatoid arthritis, idiopathic fibrosis, glomerulonephritis and damages caused by ischemia and reperfusion is disclosed therein.

Compd. 2 is also specifically disclosed therein and corresponds to compound (1a) of the above document. Compd. 2 is a potent and selective dual CXCR1/CXCR2 non-competitive allosteric inhibitor (Bertini et al, Br J Pharmacol 2012, 165(2):436-54).

The second object of the present invention is the use of an IL-8 inhibitor as already defined above for the preparation of a medicament for the treatment and/or prevention of IC/PBS and/or OAB. According to a preferred embodiment of the present invention, said IC/PBS and/or OAB is induced by anticancer therapy, such as chemotherapy or radiotherapy to the pelvis.

The third object of the present invention is a method for the treatment and/or prevention of IC/PBS or OAB in a subject comprising the step of administering to the subject in need thereof a therapeutically effective amount of an IL-8 inhibitor as already defined above. According to a preferred method object of the present invention, IC/PBS and/or OAB is induced by anticancer therapy, such as chemotherapy or radiotherapy.

As used herein, a "therapeutically effective amount" refers to an amount sufficient to achieve treatment or prevention of the disease. Determination of the effective amounts is well within the capability of those skilled in the art based upon the achievement of a desired effect. An effective amount will depend on factors including, but not limited to, the weight of a subject and/or the degree to which the disease or unwanted condition from which a subject suffers. The terms "treatment" and "prevention" as used herein refer to the eradication/amelioration or prevention/delay in onset, respectively, of the disorder being treated or of one or more of the symptoms associated thereof, notwithstanding the fact that the patient may still be afflicted with the underlying disorder.

The fourth object of the present invention is a pharmaceutical composition comprising an IL-8 inhibitor as defined above for use in the treatment and/or prevention of IC/PBS or OAB in association with pharmaceutically suitable excipients.

Preferably, said pharmaceutical composition further comprises at least one further pharmaceutically active compound.

The fifth object of the present invention is a product or kit comprising:
A) an IL-8 inhibitor as defined above for use in the treatment and/or prevention of IC/PBS, preferably cystitis induced by anticancer therapy, or OAB or a pharmaceutical composition as defined above, and
B) at least one further pharmaceutically active compound
A) and B) being two separate formulations for simultaneous, separate or sequential use.

According to one preferred embodiment of the fourth or fifth object of the invention, said further pharmaceutically active compound of said pharmaceutical composition or kit is an active compound useful for the prevention and treatment of IC/PBS or OAB. Preferably, according to this embodiment, said further pharmaceutically active compound is a TRPV1 antagonist.

According to an alternative preferred embodiment of the fourth or fifth object of the invention said pharmaceutically active compound is an active compound that induces, as an undesired effect, IC/PBS or OAB. Preferably, said active compound is an anticancer agent, preferably selected from cyclophosphamide, the Bacillus Calmette-Guérin to be instilled directly into the bladder [Lamm et al Eur Urol Suppl 2010, 9: 715; Hall et al J Urol 2007, 178: 2314], mitomycin C, adriamycin [Isaka et al Cancer Chemother 1992, 30: S41-S44], or tiaprofenic acid (surgam) [Buchbinder et al J Clin Epidemiol 2000, 53: 1013].

For the purpose of the present invention, the inhibitors of IL-8 according to the present invention are formulated in pharmaceutical compositions suitable for use by oral formulation, such as tablets, capsules, syrups, preferably in the form of controlled release formulations, or by parenteral administration, preferably in the form of sterile solutions suitable for intravenous or intramuscular administration. The pharmaceutical compositions can be prepared according to conventional methods, for example as disclosed in Remington, "The Science and Practice of Pharmacy", $21^{st}$ ed. (Lippincott Williams and Wilkins).

Preferably, the amount of Compd. 1 or its pharmaceutically acceptable salt in each of the above-mentioned administration forms will be such as to provide between 3 and 5 mg compound or salt/kg body weight, while the amount of Compd. 2 or its pharmaceutically acceptable salt will be such as to provide between 200 and 300 mg compound or salt/kg body weight. In any case, the regimen and amount of medicament to be administered will be determined by the physician according to the human pharmacokinetics.

The invention will be further illustrated in greater details in the following experimental section.

Experimental Section

Cyclophosphamide (CYP)-Induced Cystitis Model

Cyclophosphamide (CYP) is a nitrogen mustard-type chemotherapeutic agent, which is used for the treatment of neoplastic diseases. CYP is converted in the kidney to acrolein, which accumulates in the bladder, causing hemorrhagic cystitis leading to bladder overactivity (OAB) and irritative voiding symptoms, which resemble those typical of painful bladder syndrome (PBS), interstitial cystitis (IC) and OAB (Stillwell et al, Cancer 1988, 61: 451; Juszczak et al Folia Med Cracov. 2007, 48: 113).

Therefore, cyclophosphamide (CYP) induced cystitis is a well-characterized model of acute and chronic inflammatory cystitis in rodents and it is commonly used as an experimental model for IC/PBS and OAB.

Female Sprague Dawley rats (Crl:CD(SD)BR, 250-350 g) from Charles River Italy were used in these experiments. Animals were housed with free access to food and water and maintained on a forced 12 hours light-dark cycle at 22-24° C. for at least one week before the experiments were carried out. The animals were handled according to internationally accepted principles for care of laboratory animals (E.E.C. Council Directive 86/609, O. J. n°L358, Dec. 18, 1986).

Von Frey monofilaments of different forces (Ugo Basile, Comerio, VA-Italy) were utilized through the experiments.

Cyclophosphamide, 75 mg/kg i.p. for 3 times, every $3^{rd}$ day, was dissolved in distilled water and administered to animals by i.p. route (volume 5 mL/kg). Appropriate weight of Compd. 1 or Compd. 2 was dissolved in saline, all doses of test compounds were administered by oral gavage (volume 2 mL/kg).

On the day of the experiment, each rat was placed individually in a clear plastic testing box with a grid floor and allowed to acclimatize for at least 10 min. Visceral sensitivity in response to mechanical stimuli was determined using Von Frey monofilaments (1-2-4-8-15-26-60-100 g) applied in the lower abdominal area (close to the urinary bladder) and on both hind paws plantar surface (to evaluate referred pain).

Each Von Frey monofilament was applied 5 times at the level of abdomen and 3 times at the level of each paw, in an ascending order of strength at interval of 5 sec. A stimulus-induced response was considered positive when the paw was sharply withdrawn, paw licking occurred, or the animal flinched upon removal of the filament.

Example 1

Effects of Acute Administration in CYP-Induced Visceral Pain in Rats

Behavioral testing on animals was performed at 3 different times:
  before CYP administration (in order to acquire basal values)
  after CYP administration, before treatment with the test compound, to verify the pathology (in order to acquire pre-treatment values)
  after CYP administration, after treatment (in order to acquire post-treatment values)

Behavioral evaluations, to test the effect of Compd. 1, Compd. 2 or vehicle, were performed 2 hours after the administration of compounds. The test was performed in blind.

Chronic treatment with CYP (75 mg/kg i.p. for 3 times, every $3^{rd}$ day), induces a strong decrease in withdrawal thresholds to noxious stimulus measured at the level of low abdomen and hind-paws.

Basal withdrawal threshold mean values in the different groups utilized ranged between 69.8 and 81.2 grams in abdomen, and between 36.2 and 44.2 grams in hind paws. No statistically significant differences between the basal and pre-treatment values in the different groups of treatment were found. In the control group, nociceptive thresholds of abdomen and hind-paws were not altered after the treatment with vehicle (FIGS. 1-5).

Compd. 1 and Compd. 2 at doses of 10 and 30 mg/kg or vehicle were orally administered to rats 2-9 days after last CYP administration, when painful symptoms were well established.

Figure 1:
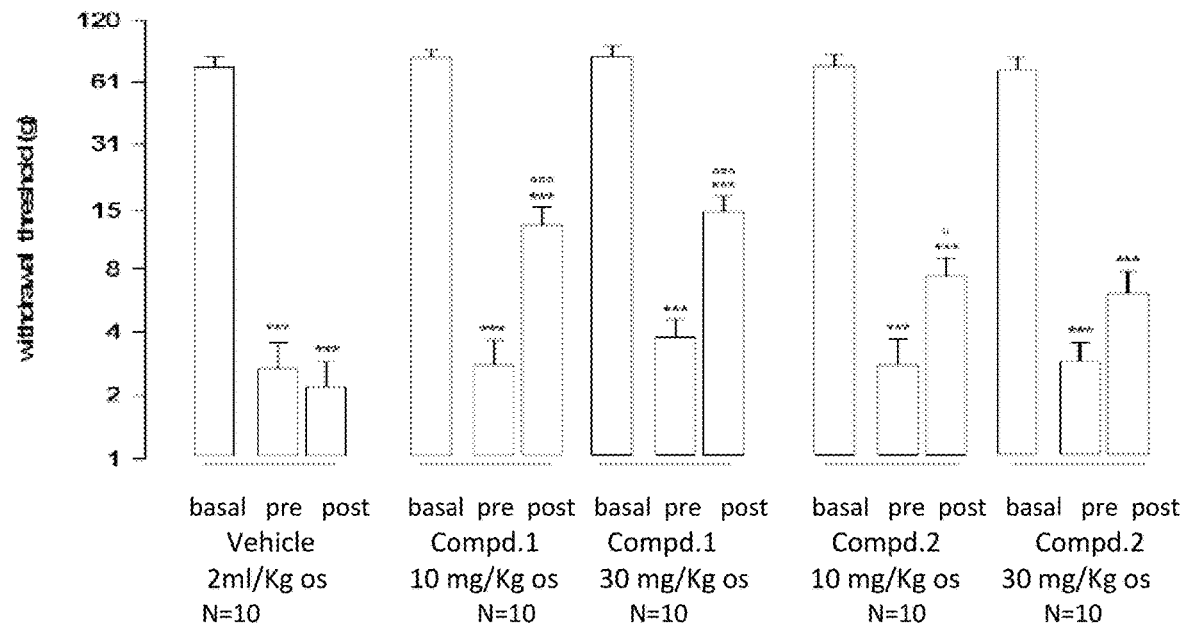
Figure 2:
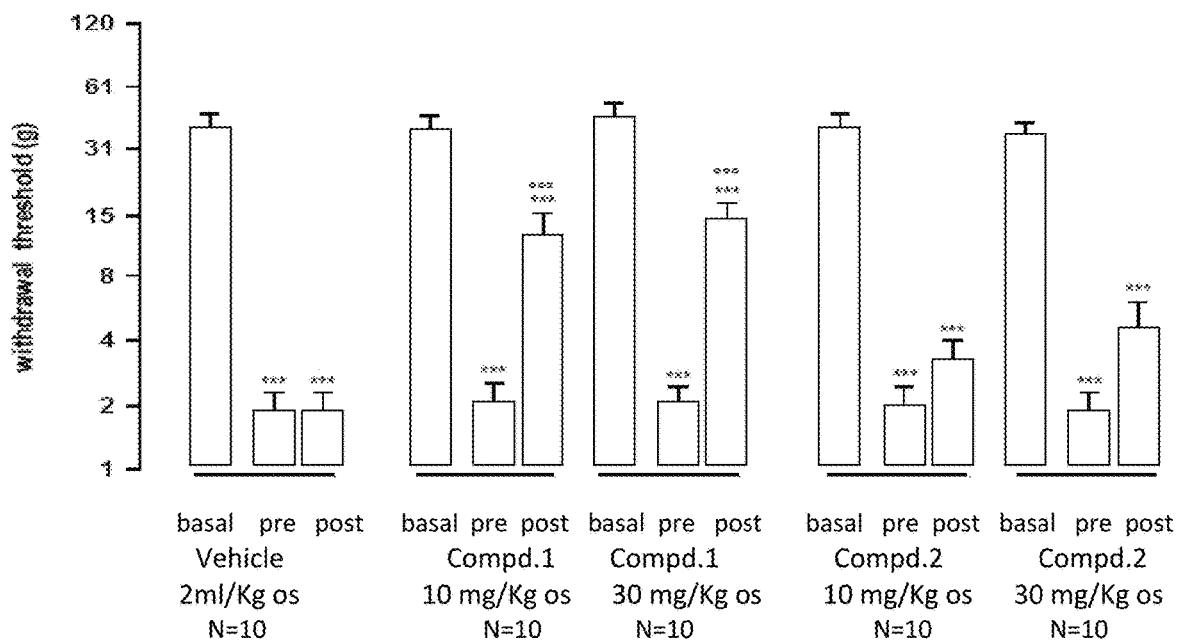

Compd. 1 at the doses of 10 and 30 mg/kg p.o. induced a statistically significant increase in mechanical threshold in both the abdomen and paws area and the effect of the higher dose was not significantly different from that induced by the lower one (FIGS. 1-2).

Compd. 2 at the dose of 30 mg/Kg p.o. induced a statistically significant increase in mechanical threshold in both the abdomen and paws area, while at 10 mg/Kg p.o. induced a statistically significant increase in mechanical threshold only in the abdomen (FIGS. 1-2).

Figure 3:
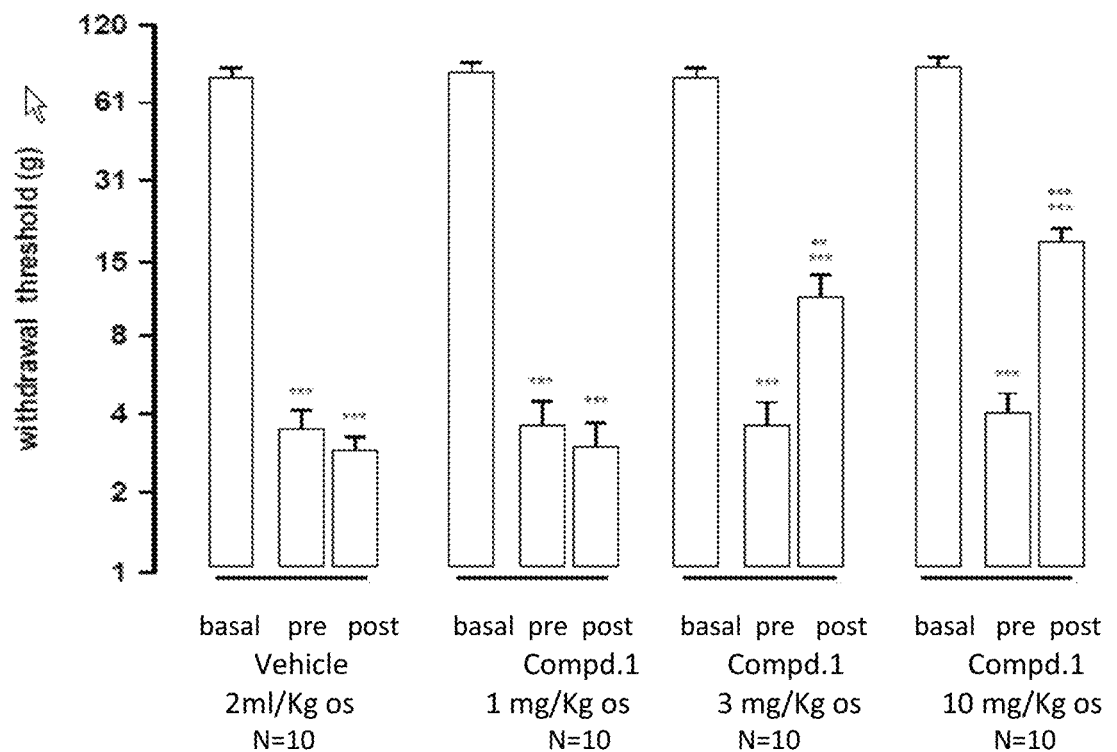
Figure 4:
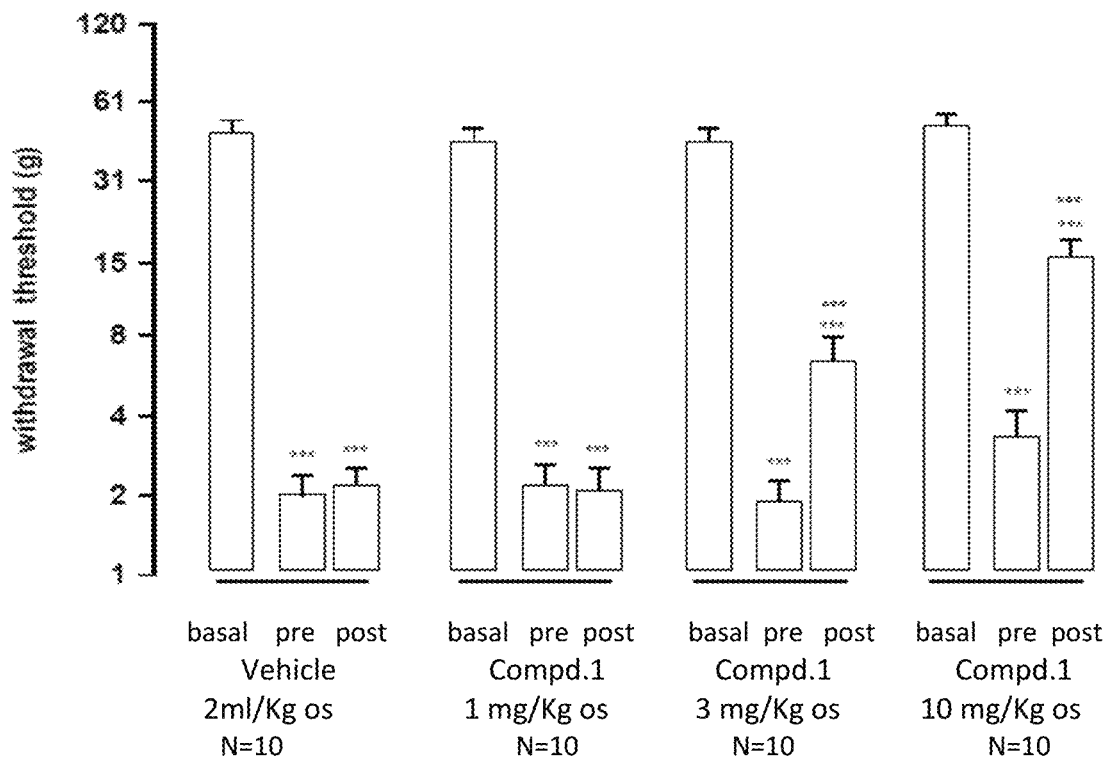
Figure 5:
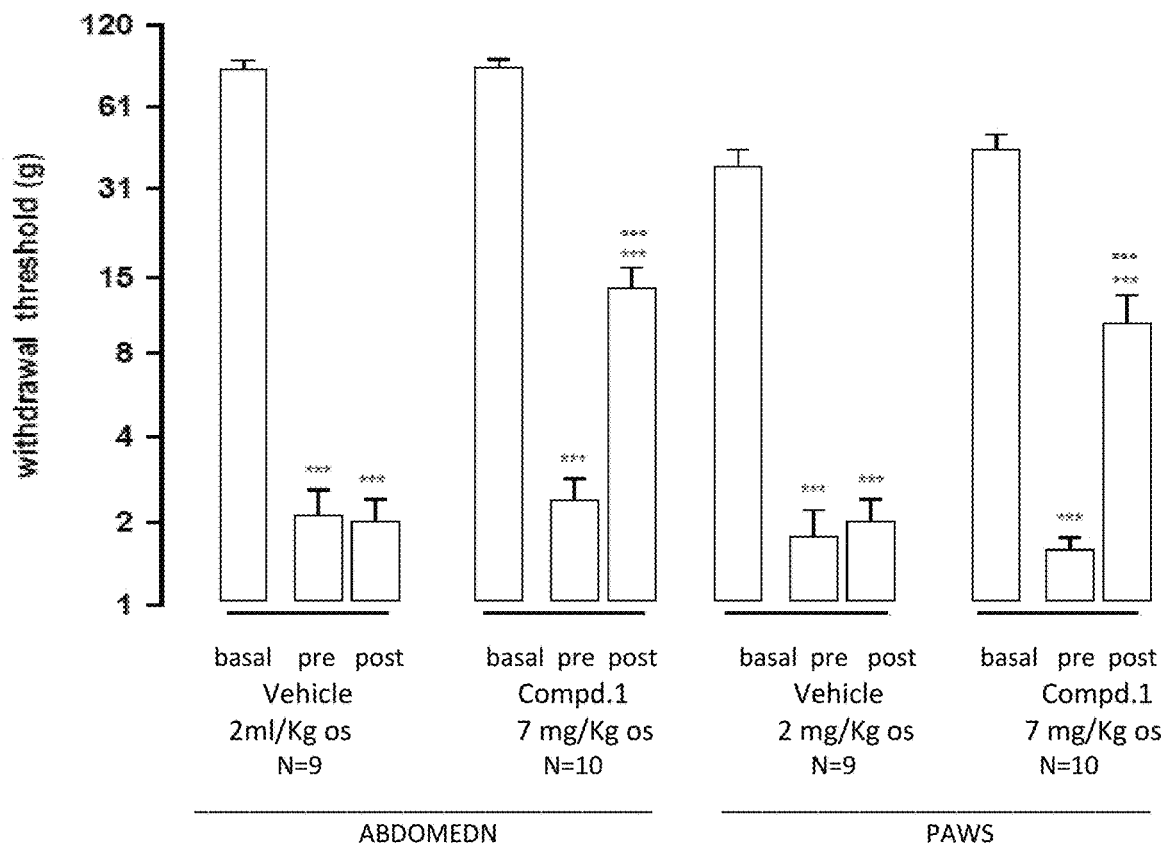

In order to evaluate the MED of Compd. 1, lower doses were further tested: 1, 3, 7 and 10 mg/kg. Compd. 1 showed a dose-dependent effect: particularly, at the doses of 7 and 10 mg/kg it showed a good efficacy, inducing a statistical significant reduction of painful hypersensitivity in both the abdominal and plantar surface; at the dose of 3 mg/kg it caused a statistical significant increase of mechanical threshold in both the areas evaluated. The withdrawal thresholds after treatment with the dose of 1 mg/kg were not significantly different from the pretreatment values, therefore suggesting that the MED of Compd. 1 is 3 mg/kg (FIGS. 3-5).

The above data demonstrate that the administration of Compd. 1 at the doses of 10 and 30 mg/kg produce a significant increase in mechanical thresholds both in the abdomen and hind-paws plantar surface; as the efficacy is similar for both the tested doses, a plateau of the effect can be hypothesized and thus a MED of 3 mg/kg has been identified.

Example 2

Effects of the Chronic Administration in CYP-Induced Visceral Pain in Rats
Behavioral Testing was Performed at 4 Different Times:
- before CYP administration (in order to acquire basal values)
- after CYP administration and before treatment, to verify the pathology (in order to acquire pre-treatment values)
- after chronic treatment, about 18 hours after last administration of Compd. 1 (in order to acquire post-treatment values).
- after chronic treatment, 2 hours after the last administration of Compd. 1 (in order to acquire post-treatment values after chronic+acute administration)

Repeated treatment with CYP (75 mg/kg i.p. for 3 times, every 3rd day), induces a strong decrease in withdrawal thresholds to noxious stimulus measured at the level of low abdomen and hind-paws.

The oral dose of 7 mg/kg of Compd. 1 was chosen on the basis of the evaluation reported in Example 1: in fact, this dose was able to reduce visceral hypersensitivity in a more sustained manner than MED (3 mg/kg).

Compd. 1 or vehicle was administered p.o. to animals twice daily (according to the pharmacokinetic profile of the compound) for 6 days, starting from 24 hours after last treatment with CYP, when painful symptoms were well established. Nociceptive hypersensitivity was evaluated about 18 hours after the last administration of Compd. 1 (or vehicle) in order to evaluate the effect of chronic administration, or a further dosage of compound was administered and evaluation carried out 2 hours thereafter, in order to compare with acute protocol, described in Example 1.

Figure 6:
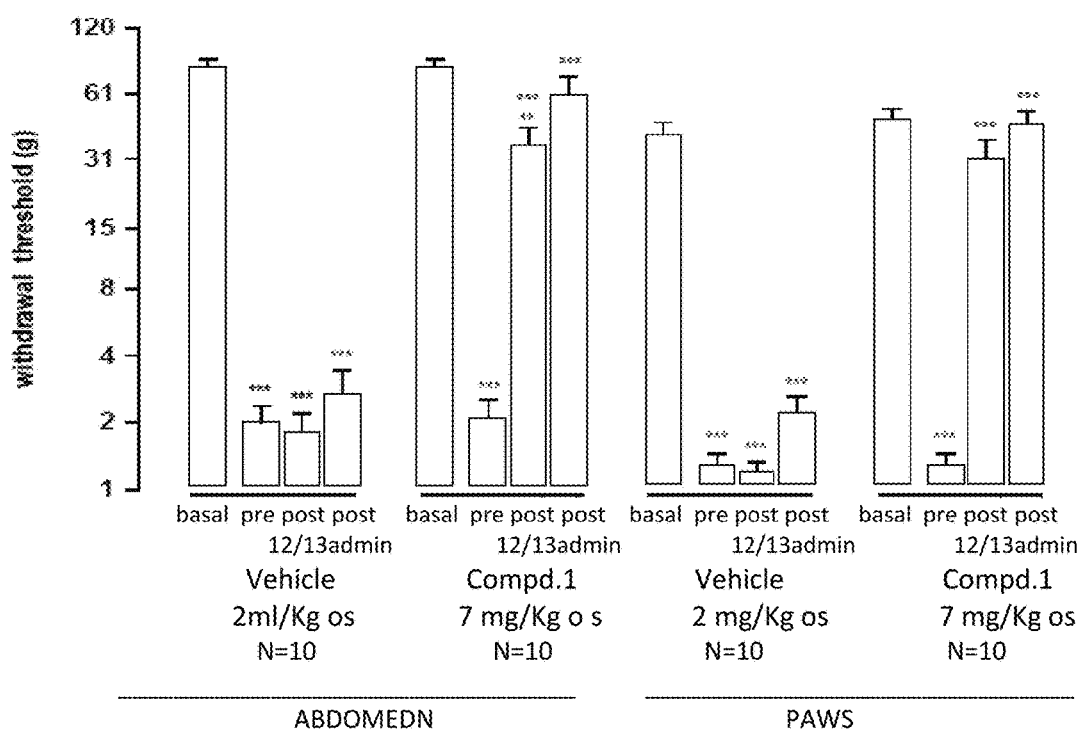

No statistically significant differences between the basal and pre-treatment values in the different groups of treatment were observed. In the control group, nociceptive thresholds of abdomen and hind-paws were not altered after the treatment with vehicle (FIG. 6).

The chronic administration of Compd. 1 (7 mg/kg twice daily, p.o., for 6 days) produced an almost complete recovery of withdrawal thresholds in the abdomen and completely reversed the nociceptive hypersensitivity in hind-paws plantar surface. Compd. 1 fully abolished the painful visceral symptoms in both evaluated areas 2 hours following the last administration (FIG. 6).

The above data demonstrate that, when IC/PBS symptoms are induced by repeated CYP administration, the chronic treatment with Compd. 1 produces an almost complete increase in withdrawal thresholds in the abdomen and completely reverses the nociceptive hypersensitivity in hind-paws plantar surface. In the same experimental conditions, morphine administered at the dose of 3 mg/kg s.c. produced similar analgesic effect of Compd. 1, but caused marked and well known side effects (sedation, respiratory effects). Finally, Compd. 1 fully abolished the painful visceral symptoms in both evaluated areas 2 hours following the last administration.

Example 3

Microscopic Examination of Urinary Bladders

At the end of the efficacy study of chronic administration, the urinary bladders were opened, placed in 10% buffered formalin and stored at room temperature until hystomorphological analysis.

Treatment with Compd. 1 for 6 days (7 mg/kg, oral, twice a day) of female rats after the induction of urinary bladder cystitis with CYP (75 mg/kg, i.p., three times) clearly reduced or reversed the inflammatory, degenerative and proliferative lesions caused by the treatment. The induced lesions consisted of apoptosis, erosions of the mucosa, mitoses of the mucosal cells, mucosal hyperplasia, infiltration of inflammatory cells and micro-hemorrhages. Caspase 3 and caspase 9 expression (markers of apoptosis) as well as Ki67 expression (marker for cell proliferation) were reduced in the group treated with Compd. 1.

CYP alone: Treatment with CYP alone induced apoptosis of the epithelial cells of the mucosa in all animals in the group. Mitoses were present in the epithelial cells of the basal layers in half of the animals in the group and were associated to a mucosal hyperplasia (diffuse or multifocal) with the exception of one rat where no corresponding hyperplasia was seen. Minimal infiltration of inflammatory cells (mostly lymphocytes and neutrophils), micro-hemorrhages of the mucosa, submucosa or muscle layers, and mucosal erosions were also present in about 50% of the animals (Table 1).

The microscopic examination showed erosion and hyperplasia of the mucosa and infiltration of inflammatory cells in the submucosa.

CYP+Compd. 1: In the group treated with Compd. 1 after the pre-treatment with CYP, the animals presented a pronounced reduced incidence and severity of apoptosis (3/10 rats versus 10/10 in the CYP alone group). Few inflammatory cells were detected in the submucosa of one animal. Mitoses in the epithelial cells were absent as well as erosion of mucosa and micro-hemorrhages, thus resulting in a clear protective/reparative effect of the test item. Mucosal hyperplasia was only present in one animal (Table 1).

Immunohistochemistry showed a higher grade of positivity for caspases 3 and 9 in the CYP group vs CYP+Compd. 1 group, indicating a higher rate of the apoptotic process in the CYP group.

Ki67, a very well established marker for cell proliferation, has a lower grade of positivity in CYP+Compd. 1 group than in CYP group. The observed reductions in the group CYP+Compd. 1 are biologically relevant.

The microscopic examination showed mucosa with normal appearance with no inflammatory cells in the submucosa.

TABLE 1

Incidence of Relevant Microscopic Findings

| Groups | CYP | CYP + Compd. 1 | U Mann-Whitney test |
|---|---|---|---|
| N. animals/group | 10 | 10 | |
| Urinary Bladder | | | |
| Apoptosis epithelial cell | 10 | 3 | P = 0.0003 |
| Mitoses | 5 | 0 | P = 0.0124 |
| Erosion, mucosa | 5 | 0 | P = 0.0118 |
| Mucosal Hyperplasia | 4 | 1 | P = 0.0301 |
| Micro-hemorrhage | 3 | 0 | P = 0.0671 NS |
| Infiltration inflammatory cells | 5 | 1 | P = 0.0571 NS |

Example 4

Effects of the Acute Administration on Cystometrografic Recordings in Conscious Rats with CYP-Induced Cystitis

Female Sprague Dawley rats (Crl:CD(SD)BR, 250-350 g bw) from Charles River Italy were used in these experiments. Animals were housed with free access to food and water and maintained on a forced 12 hours light-dark cycle at 22-24° C. for at least one week before the experiments were carried out. The animals were handled according to internationally accepted principles for care of laboratory animals (E.E.C. Council Directive 86/609, O. J. n°L358, Dec. 18, 1986).

The following instruments were utilized through the experiments:

Peristaltic pumps Gilson minipuls 2 or Gilson minipuls 3
Pressure transducers Statham P23 XL
Data acquisition Biopac System.

Rats, anaesthetized with equithensin solution (2 ml/kg i.p.), were placed in a supine position and an approximately 10 mm midline incision was made in the shaved and cleaned abdominal wall. The urinary bladder was gently freed from adhering tissues, emptied and then cannulated, via an incision at the dome, with a polyethylene cannula (Portex, ID 0.58 mm, OD 0.96 mm), which was permanently sutured with silk thread. The cannula was exteriorized through a subcutaneous tunnel in the retroscapular area, where it was connected with a plastic adapter, in order to avoid the risk of removal by the animal.

After the surgical procedure, the animals were treated by i.p. route with CYP 175 mg/kg for induction of cystitis. For drugs testing, rats were utilized one day after catheter implantation at about 24 hours after administrations CYP.

On the day of the experiment, the rats (fasted overnight) were placed in Bollman's cages; after a stabilization period of 20 min, the free tip of the cannula was connected by a T-shape tube to a pressure transducer and to a peristaltic pump for a continuous infusion of saline solution (room temperature) into the urinary bladder, at the constant rate of 0.05 ml/min. This procedure, termed cystometry, allows the detection of continuous cycles of filling and voiding of the bladder named cystometrograms.

From the cystometrograms acquired by the Biopac System and recorded on a PC the Bladder Volume Capacity (BVC) parameter was calculated as volume capacity, defined as volume (in ml) infused into the bladder and necessary to induce detrusor contraction followed micturition.

Basal BVC was evaluated as mean values from the cystometrograms recorded in 30-60 minutes of time prior the treatment ("BASAL"). Then the bladder infusion was stopped, the animals were treated orally with the test compound or vehicle and, after restarting continuous bladder filling with saline for 4 or 5 hours, BVC values after administration were collected.

BVC parameters were recorded from the cystometrogram over a 4/5 hours period post-dose.

Drugs were orally administered to fasted rats at doses of 10, 20 and 30 mg/kg dissolved in saline, 24 hours after treatment with CYP (175 mg/5 ml/kg i.p.).

In general, following CYP treatment, animals showed a decrease of BVC, corresponding to a reduction around 30-50% in comparison with the values before CYP treatment.

In the control group treated with vehicle, the continuous infusion with saline induced a slight variation (up to about 15%) of BVC values during all the experimental session.

In order to obtain more homogeneous groups, only rats having BVC values lower than 0.5 ml, corresponding to a reduction of 30-50% in comparison with BVC value (obtained in previous study) before CYP treatment, were included in the study. Basal BVC mean values were between 0.21 and 0.36 ml, whereas basal MP mean values were between 57.4 and 82.7 mmHg. No statistically significant differences for all the two considered parameters were observed between the basal values among groups.

Figure 7:
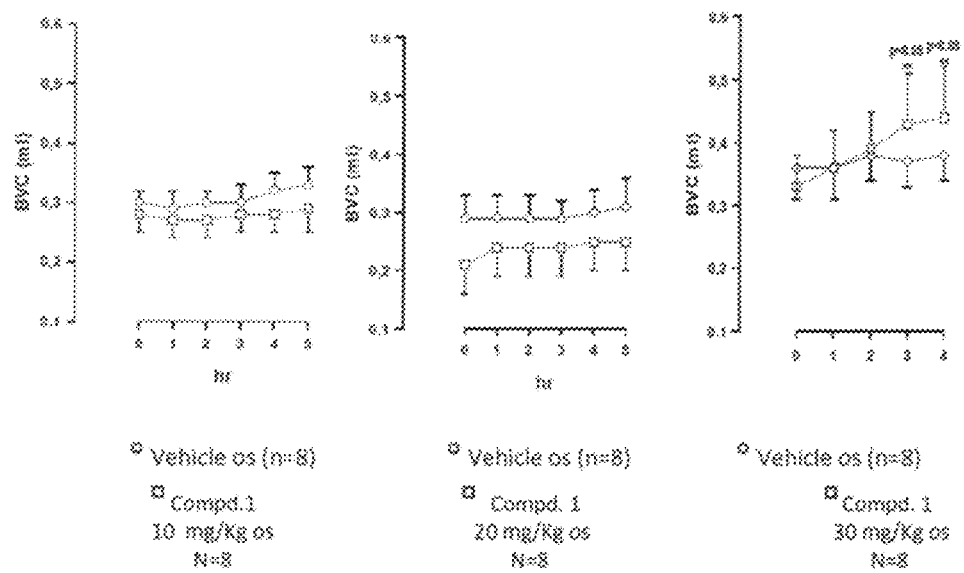
FIG. 7 shows the effect of oral administration of vehicle and Compound 1 (Compd. 1), administered at a dosage of 10, 20 and 30 mg/kg, on the bladder volume capacity (BVC) after CYP treatment, tested as described in Example 4. Data are expressed as Mean values±S.E. p<0.01, *p<0.001 versus basal values; °°°p<0.001, versus pre-treatment values (one way ANOVA with Tukey's test).

Oral administration of 10 mg/kg Compd. 1 did not induce any changes of BVC. Compd. 1 at 20 mg/kg showed a moderate increase of BVC statistically different from vehicle and pre-drug treatment at 4 and 5 hours. The highest dose tested of Compd. 1, namely 30 mg/kg, induced a sustained increase of BVC, up to +40%. These changes resulted statistically different from basal values, as well as the vehicle group, at 3 and 4 hours after treatment (FIG. 7).

Figure 8:
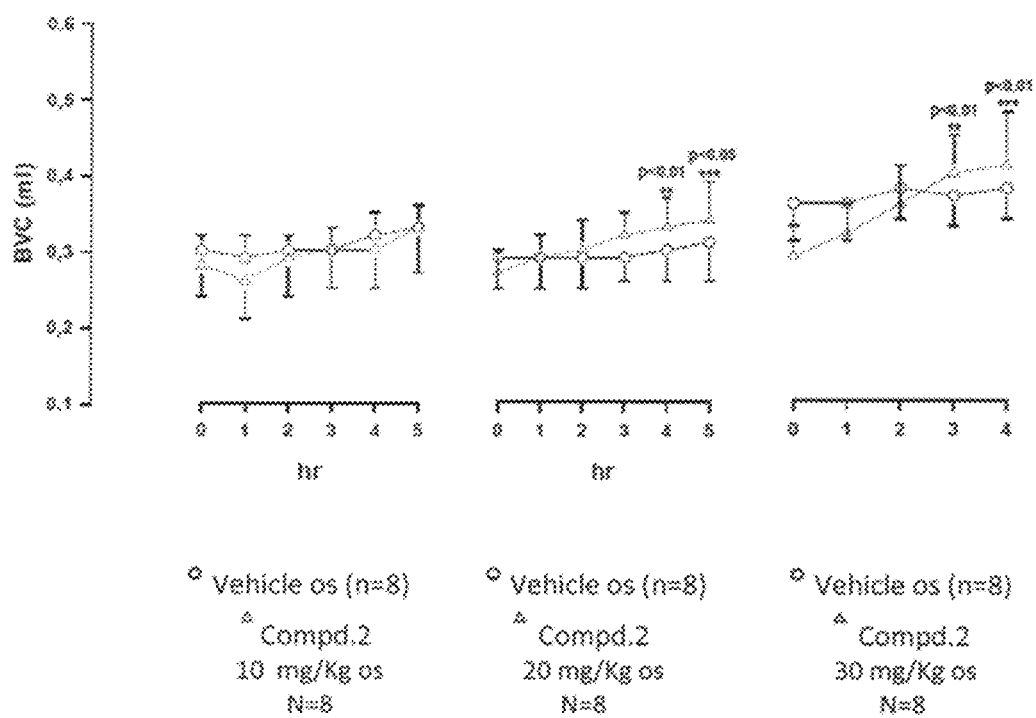
FIG. 8 shows the effect of oral administration of vehicle and Compound 2 (Compd. 2), administered at a dosage of 10, 20 and 30 mg/kg, on the bladder volume capacity (BVC) after CYP treatment, tested as described in Example 4. Data are expressed as Mean values±S.E. p<0.01, *p<0.001 versus basal values; °°°p<0.001, versus pre-treatment values (one way ANOVA with Tukey's test).

Also Compd. 2 at the dose of 20 and 30 mg/Kg showed efficacy on BVC (FIG. 8). The above data demonstrate that Compd. 1 after oral administration in conscious rats pretreated with CYP, at the doses of 20 and 30 mg/kg is able to increase the BVC, with a long-lasting effect statistically and significantly different from the vehicle. At the same dose the molecule is inactive on MP.

Example 5

Effects of Compd. 1 Chronic Preventive Treatment in a CYP-Induced Visceral Pain Model in Rats; Comparison with Mesna.

The effect of chronic preventive administration of Compd. 1 in a visceral pain model induced by repeated administration of cyclophosphamide (CYP) in conscious rats was evaluated.

The oral dose of 7 mg/kg of Compd. 1 was chosen on the basis of previous evaluations. Compd. 1 or vehicle was orally administered to animals twice daily (according to the PK profile of the molecule) for 7 days. Mesna_or vehicle was intraperitoneally administered several times a day for 3 days (when CYP was administered).

Repeated treatment with CYP (75 mg/kg i.p. for 3 times, every $3^{rd}$ day), induced a strong decrease in withdrawal thresholds to noxious stimulus measured at the level of low abdomen and hind-paws. Nociceptive hypersensitivity was evaluated. In the control group, nociceptive thresholds of abdomen and hind-paws were not altered after the treatment with vehicle.

Behavioral testing was performed at 4 different times:
before CYP administration (in order to acquire basal values)
after CYP administration and before treatment with the tested compound, to verify the pathology (in order to acquire pre-treatment values)
after treatment, 42 or 48 hours from the last administration of Compd. 1 or Mesna.

At the end of the study, the urinary bladders were opened, placed in 10% buffered formalin and stored at room temperature until completion of hystomorphological analysis (see Example 6 below).

The basal and pre-treatment values in the different groups of treatment do not show any statistically significant difference.

In the control group, nociceptive thresholds of abdomen and hind-paws were not altered after the treatment with vehicle (FIGS. 9 and 10).

The chronic preventive administration of Compd. 1 (7 mg/kg twice daily, p.o., for 7 days) produced an almost complete recovery of withdrawal thresholds in the abdomen and completely reversed the nociceptive hypersensitivity in hind-paws plantar surface (FIG. 9).

The chronic preventive administration of Mesna (2-mercaptoethene sulfate), a drug currently used to prevent the incidence of hemorragic cystitis induced by anticancer therapy, administered at a dosage of 12.5 mg/kg i.p. for several times a day for 3 days, did not produce a reduction of CYP-induced nociceptive behavior (FIG. 10).

Example 6

Microscopic Examination of Urinary Bladders

At the end of the efficacy study of chronic preventive administration, the urinary bladders were opened, placed in 10% buffered formalin and stored at room temperature until hystomorphological analysis.

Treatment with Compd. 1 administered 12 hours before and twice per day from the first day of CYP treatment for the following 7 days, clearly reduced the inflammatory, degenerative, proliferative and hemorrhagic lesions caused by CYP, clearly highlighting the protective effect of Compd. 1. The treatment with Mesna did not exert any protective effect on the CYP-induced cystitis.

Overall these experiments show that representative examples of IL-8 inhibitors such as Compd. 1 and Compd. 2, in particular Compd. 1, are able to increase the mechanical threshold in both the abdomen and paws area after acute administration.

Moreover, chronic treatment with Compd. 1 fully abolished the painful visceral symptoms in both evaluated areas, 2 hours following the last administration. In the same experimental conditions, morphine administered at the dose of 3 mg/kg s.c. produced similar analgesic effect than Compd. 1, but caused marked and well known side effects (sedation, respiratory effects). Systemic gabapentin yielded a partial maximum antinociceptive effect when administered at the dose of 40-80 mg/kg p.o.

In addition, Compd. 1 and Compd. 2, orally administered at 20 and 30 mg/kg, were able to increase the BVC and pre-treatment with Compd. 1 resulted to have antinociceptive effect in comparison to Mesna. Finally, the antihyperalgesic effect of Compd. 1 up to 10 days after discontinuation of treatment was evaluated and, as main results, it was observed that animals treated with Compd. 1 has a body weight recovery faster than vehicle-treated animals, in agreement with the evolution of painful symptoms and, in general, the treated animals were healthier than vehicle-treated ones with an observed increase also in survival (65% vs. 50% of vehicle-treated).

The data obtained clearly show that Compd. 1 and Compd. 2, but mainly Compd. 1, are efficacious in animal models of IC/PBS and may be proposed for further investigation to support the use in humans.

Example 7

KC/GRO-α Plasma Content after Preventive Treatment with Compd 1 in a CYP-Induced Cystitis Model in Rats The effect of chronic preventive administration of Compd. 1 on KC/GRO-α plasma content in a CYP-induced cystitis model in conscious rats was evaluated.

To elicit cystitis, rats received intraperitoneal (i.p.) injections of CYP (75 mg/Kg every third day for three times). A single high dose of Compd. 1 (20 mg/kg) was orally administered 12 hours before the first CYP treatment; subsequently Compd. 1 (7 mg/kg p.o.) was administered twice a day for 7 days (from day 1 to day 7 from the first CYP administration). The oral dose of 7 mg/kg of Compd. 1 was chosen on the basis of previous evaluations. Animals blood was collected at day 7 (the same day of the last CYP treatment) at day 8 (about 24 hrs after last CYP administration) and at day 9 (about 48 hrs after last CYP administration). Each experimental group was composed of 10 animals, 10 animals treated with CYP+vehicle compound, 10 animals treated with CYP+Compd. 1, and 10 animals (sham) treated with CYP vehicle+vehicle compound.

The same animal was subjected to 3 blood serial samplings in order to evaluate the time-course of inflammatory mediators content. After thawing and centrifuge to remove any aggregates and lipid residues that could interfere with the reading, the samples were evaluated through quantitative analysis of KC/GRO-α.

The time dependent changes in blood GROa/KC content following CYP administration and effect of the pre-treatment with Compd 2. are shown in FIG. 11.

In the present study, disease progression was profiled by the CYP-induced time dependent changes in blood GRO-α/KC levels related to sham values. In this experimental session, blood GRO-α/KC levels increased in a time dependent fashion, reaching a peak at day 9 after the first CYP injection. The pre-treatment of Compd. 1 significantly reduces GRO-α/KC blood levels at day 9.

These data showed that also in the described rat model of CYP-induced cystitis, besides the marked bladder overactivity, bladder inflammation and visceral pain, a robust systemic inflammatory response is evident. As GRO-α/KC is a representative pro-inflammatory chemokine that is related to the development of CYP-induced cystitis and could potentially have a prognostic role in IC/PBS patients.

The invention claimed is:
1. A method of treating interstitial cystitis/painful bladder syndrome (IC/PBS) and/or over active bladder (OAB) in a subject in need thereof, comprising administration of an effective amount of a CXCR1 inhibitor or a dual CXCR1 and CXCR2 inhibitor, wherein the CXCR1 inhibitor or dual CXCR1 and CXCR2 inhibitor is a compound of formula (I)

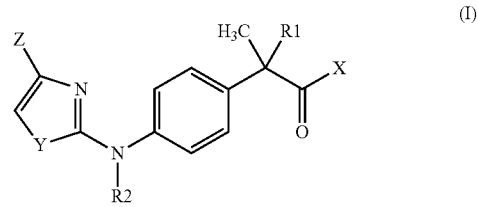

wherein
R1 is hydrogen;
X is OH;
R2 is hydrogen or linear $C_1$-$C_4$ alkyl;
Y is a heteroatom selected from S, O and N; and
Z is selected from linear or branched $C_1$-$C_4$ alkyl, linear or branched $C_1$-$C_4$ alkoxy, halo $C_1$-$C_3$ alkyl and halo $C_1$-$C_3$ alkoxy;
or a pharmaceutically acceptable salt thereof.

2. The method according to claim 1, wherein the IC/PBS and/or over active bladder (OAB) is induced by anticancer therapy or radiotherapy to the pelvis.

3. The method according to claim 1, wherein the compound of formula (I) is selected from (R,S)-2-(4-{[4-(trifluoromethyl)-1,3-thiazol-2-yl]amino}phenyl)propanoic acid and (2S)-2-(4-{[4-(trifluoromethyl)-1,3-thiazol-2-yl]amino} phenyl) propanoic acid, or a sodium salt thereof.

4. The method according to claim 1, wherein the compound of formula (I) is administered as a pharmaceutical composition comprising the compound of formula (I) and at least one pharmaceutically acceptable excipient.

5. The method according to claim 4, wherein the pharmaceutical composition further comprises at least one further pharmaceutically active compound.

6. The method according to claim 5, wherein the further pharmaceutically active compound is an active compound useful for the prevention and treatment of IC/PBS and/or OAB.

7. The method according to claim 6, wherein the further pharmaceutically active compound is a TRPV1 antagonist.

8. The method according to claim 5, wherein the further pharmaceutically active compound is a drug that induces, as an undesired effect, IC/PBS or OAB.

9. The method according to claim 8, wherein the further pharmaceutically active compound is selected from cyclophosphamide, *Bacillus* Calmette-Guérin to be instilled directly into the bladder, mitomycin C, Adriamycin or tiaprofenic acid.

10. A method of preventing interstitial cystitis/painful bladder syndrome (IC/PBS) and/or over active bladder (OAB), wherein the IC/PBS and/or OAB is induced by anticancer therapy or radiotherapy to the pelvis, in a subject undergoing anticancer therapy or radiotherapy to the pelvis, comprising administration of an effective amount of a CXCR1 inhibitor or a dual CXCR1 and CXCR2 inhibitor, wherein the CXCR1 inhibitor or dual CXCR1 and CXCR2 inhibitor is a compound of formula (I)

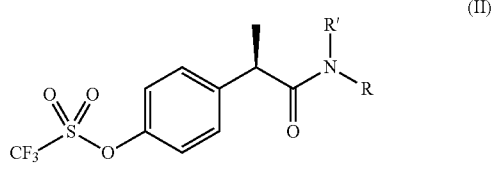

(II)

wherein

R1 is hydrogen;

X is OH;

R2 is hydrogen or linear $C_1$-$C_4$ alkyl;

Y is a heteroatom selected from S, O and N; and

Z is selected from linear or branched $C_1$-$C_4$ alkyl, linear or branched $C_1$-$C_4$ alkoxy, halo $C_1$-$C_3$ alkyl and halo $C_1$-$C_3$ alkoxy;

or a pharmaceutically acceptable salt thereof.

11. The method according to claim 10, wherein the compound of formula (I) is selected from (R,S)-2-(4-{[4-(trifluoromethyl)-1,3-thiazol-2-yl]amino}phenyl)propanoic acid and (2S)-2-(4-{[4-(trifluoromethyl)-1,3-thiazol-2-yl]amino}phenyl)propanoic acid, or a sodium salt thereof.

12. The method according to claim 10, the compound of formula (I) is is administered as a pharmaceutical composition comprising the compound of formula (I) and at least one pharmaceutically acceptable excipient.

13. The method according to claim 12, wherein the pharmaceutical composition further comprises at least one further pharmaceutically active compound.

14. The method according to claim 13, wherein the further pharmaceutically active compound is an active compound useful for the prevention and treatment of IC/PBS and/or OAB.

15. The method according to claim 14 wherein the further pharmaceutically active compound is a TRPV1 antagonist.

16. The method according to claim 13, wherein the further pharmaceutically active compound is a drug that induces, as an undesired effect, IC/PBS or OAB.

17. The method according to claim 16, wherein the further pharmaceutically active compound is selected from cyclophosphamide, *Bacillus* Calmette-Guérin to be instilled directly into the bladder, mitomycin C, Adriamycin or tiaprofenic acid.

* * * * *

UNITED STATES PATENT AND TRADEMARK OFFICE
CERTIFICATE OF CORRECTION

| | | |
|---|---|---|
| PATENT NO. | : 12,150,933 B2 | Page 1 of 1 |
| APPLICATION NO. | : 15/743721 | |
| DATED | : November 26, 2024 | |
| INVENTOR(S) | : Marcello Allegretti et al. | |

It is certified that error appears in the above-identified patent and that said Letters Patent is hereby corrected as shown below:

In the Claims

Claim 10, Column 17, Lines 32-40:

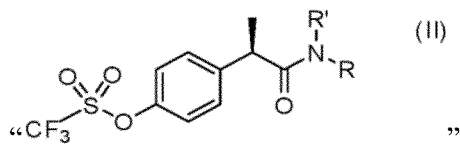

Should read:

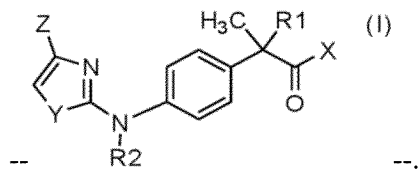

Claim 12, Column 18, Line 18:
Insert --wherein-- before "the".

Signed and Sealed this
Thirteenth Day of May, 2025

Coke Morgan Stewart
*Acting Director of the United States Patent and Trademark Office*